United States Patent
Miki et al.

(10) Patent No.: US 7,244,250 B2
(45) Date of Patent: Jul. 17, 2007

(54) SUCTION CATHETER

(75) Inventors: Shogo Miki, Chigasaki (JP); Takuji Nishide, Toyonaka (JP); Masayuki Takatera, Settsu (JP); Sakiko Hanita, Ibaraki (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/520,236

(22) PCT Filed: Jul. 28, 2003

(86) PCT No.: PCT/JP03/09518

§ 371 (c)(1),
(2), (4) Date: Jan. 4, 2005

(87) PCT Pub. No.: WO2004/012604

PCT Pub. Date: Feb. 12, 2004

(65) Prior Publication Data

US 2005/0240165 A1    Oct. 27, 2005

(51) Int. Cl.
*A61M 25/00* (2006.01)

(52) U.S. Cl. .................................................. 604/528

(58) Field of Classification Search ............... 604/264, 604/272, 523, 528, 103.04, 164.13; 600/433–435, 600/585

See application file for complete search history.

(56) References Cited

U.S. PATENT DOCUMENTS

| | | | |
|---|---|---|---|
| 5,308,342 A | * | 5/1994 | Sepetka et al. ............. 604/525 |
| 5,443,457 A | | 8/1995 | Ginn et al. |
| 5,667,521 A | * | 9/1997 | Keown ..................... 606/194 |
| 5,695,507 A | * | 12/1997 | Auth et al. ................ 606/159 |
| 5,833,644 A | * | 11/1998 | Zadno-Azizi et al. ....... 604/509 |
| 5,895,405 A | * | 4/1999 | Inderbitzen ............... 606/194 |

FOREIGN PATENT DOCUMENTS

| EP | 1 201 260 A1 | 5/2002 |
|---|---|---|
| JP | 11-009683 | 1/1999 |
| WO | WO 01/068177 A1 | 9/2001 |

\* cited by examiner

*Primary Examiner*—Loan H. Thanh
(74) *Attorney, Agent, or Firm*—Hogan & Hartson LLP

(57) ABSTRACT

Provided is an aspiration catheter which does not require a large-scale device, has a largest possible aspiration lumen, and is sufficiently flexible to track tortuous blood vessels following a guidewire, thereby being easily advanced to a target site to be treated.

In the aspiration catheter, the tip of the main shaft is obliquely cut, the distal end of the guidewire shaft is positioned at the distal end of the main shaft or protrudes from the distal end of the main shaft in the distal direction, and the relationships $0.5 \leq L2/L1$ and $L2-L1 \leq 5$ mm are satisfied, wherein $L1$ is the length of the obliquely cut portion of the main shaft in the longitudinal direction of the catheter, and $L2$ is the length from the proximal end of the guidewire shaft to the distal end of the main shaft.

8 Claims, 7 Drawing Sheets

SUCTION CATHETER

RELATED APPLICATION

This application is a nationalization of PCT application PCT/JP2003/009518 filed on Jul. 28, 2003 claiming priority to Japanese Application No. 2002-225419 filed on Aug. 1, 2002.

TECHNICAL FIELD

The present invention relates to an aspiration catheter percutaneously and transluminally introduced into the body to remove by aspiration thrombi formed in the internal blood vessels and debris, such as atheromas, released in the blood vessels, by applying a negative pressure from the proximal end of the catheter.

BACKGROUND ART

Conventionally, when stenosis or occlusion occurs in vessels, such as blood vessels, and when blood vessels are blocked by thrombi, angioplasties (e.g., PTA: Percutaneous Transluminal Angioplasty and PTCA: Percutaneous Transluminal Coronary Angioplasty) are commonly performed in order to dilate narrowed areas or reopen occluded areas of blood vessels so that blood flow in the peripheries of blood vessels is improved. Many angioplasties have been performed in many medical institutions. Furthermore, in recent years, stents have been used to maintain the dilated state of narrowed areas in many cases.

A balloon catheter for PTA or PTCA is used together with a guiding catheter and a guidewire mainly for the purpose of dilating a narrowed area or occluded area of a blood vessel. In an angioplasty using the balloon catheter, first, the guiding catheter is inserted into the femoral artery and advanced through the aorta, and the tip of the guiding catheter is positioned in the opening of the coronary artery. Then, the guidewire passing through the balloon catheter is advanced beyond the narrowed area or occluded area of the blood vessel. The balloon catheter is advanced over the guidewire, and the balloon is inflated while being positioned at the narrowed area or occluded area so that the narrowed area or occluded area is dilated. The balloon is then deflated and removed from the body. The application of the balloon catheter is not limited to treatment of narrowed areas or occluded areas of blood vessels, and the balloon catheter is also useful for many other medical applications, such as insertion into blood vessels and insertion into various body cavities and tubular tissue structures.

However, when occlusion is caused by thrombi in the blood vessel, if the occluded area is dilated by the balloon catheter, there may be a possibility that the thrombi are detached from the inner wall of the blood vessel to occlude peripheral vessels downstream. In the case of the narrowed area of the blood vessel in which the lesion contains many athero-plaques, there may be a possibility that dilation by the balloon catheter leads to scattering of the athero-plaques (atheromas) to occlude peripheral vessels. When peripheral vessels are blocked as described above, even if the occluded area or narrowed area is dilated, blood is prevented from flowing into the peripheries, resulting in slow-flow or no-reflow.

When such a situation arises, in the coronary artery or the like, it is general practice to wait and see if the blood flow is recovered, but a long recovery time is required. According to circumstances, a vasodilator, such as nitroglycerin, may be administered to recover the blood flow, or a thrombolytic agent, such as urokinase, may be locally administered to dissolve the obstruction. In either case, a long recovery time is still required. When peripheral vessels are heavily occluded to produce poor hemodynamics, an auxiliary procedure, such as intra-aortic balloon pumping (IABP), may be used.

Besides the thrombolytic therapy, a method has been attempted in which thrombi are mechanically fragmented and a negative pressure is simultaneously applied from the proximal end of the catheter to remove the thrombi from the body.

However, in order to fragment a thrombus at the catheter tip, it is of course necessary to efficiently transmit the mechanical power applied from the proximal end of the catheter to the tip of the catheter. Consequently, in order to enhance the transmission of power in the catheter shaft, the entire catheter shaft must be composed of a hard material, resulting in difficulty in advancing the catheter to the target site in the blood vessel. Furthermore, since a negative pressure must be applied from the proximal end of the catheter simultaneously with the application of mechanical power, a large-scale device is required, and thus this method has not become widely used.

On the other hand, the effect of a catheter having a simple structure in which thrombi are removed by aspiration from the body by the application of a negative pressure from the proximal end has been clinically confirmed. However, the cross-sectional area of the aspiration lumen for aspiration is not sufficiently secured, and only catheters having low aspiration capability are available. The reason for this is that the catheter is advanced over the guidewire to the target site in the blood vessel. Namely, since a guidewire lumen tracking the guidewire is provided in the aspiration lumen, it is not possible to secure a sufficient cross-sectional area of the aspiration lumen.

On the other hand, in a structure in which a guidewire lumen is provided outside an aspiration lumen, the outer diameter of the aspiration catheter inevitably increases. Consequently, the inner diameter of the guiding catheter used together increases, resulting in an enormous burden to the patient.

In addition, since any of the guidewire lumens described above usually has a length of about 30 cm from the tip of the aspiration catheter, the catheter shaft lacks flexibility, resulting in poor insertability into tortuous blood vessels.

DISCLOSURE OF INVENTION

In order to overcome the problems described above, it is an object of the present invention to provide an aspiration catheter which does not require a large-scale device, secures a largest possible aspiration lumen, and is sufficiently flexible to be advanced to a target site following a guidewire and to satisfactorily track tortuous blood vessels.

As a result of intensive research conducted by the present inventors, it has been found that the problems can be overcome by an aspiration catheter having the following structure, and thus the present invention has been completed.

Namely, an aspiration catheter includes a main shaft having an aspiration lumen disposed therein, the aspiration lumen extending from the proximal end to the distal end of the main shaft; a guidewire shaft having a guidewire lumen disposed therein, the guidewire lumen following a guidewire, the guidewire shaft being disposed at the distal end of the main shaft; and a hub disposed at the proximal end of the main shaft. The tip of the main shaft is obliquely cut, the distal end of the guidewire shaft is positioned at the distal end of the main shaft or protrudes from the distal end of the main shaft in the distal direction, and the relationships $0.5 \leq L2/L1$ and $L2-L1 \leq 5$ mm are satisfied, wherein L1 is the length of the obliquely cut portion of the main shaft in the longitudinal direction of the catheter, and L2 is the length from the proximal end of the guidewire shaft to the distal end of the main shaft.

Preferably, the relationship 2 mm$\leq L1 \leq 10$ mm is satisfied. More preferably, the guidewire shaft is provided with a radiopaque marker for confirming the position of the tip of the main shaft by radioscopy.

Furthermore, at least a proximal portion of the main shaft has a flexural modulus of 1 GPa or more. More preferably, at least a distal portion of the main shaft is applied with a hydrophilic coating.

BEST MODE FOR CARRYING OUT THE INVENTION

The embodiments of the catheter of the present invention will be described in detail with reference to the drawings. However, it is to be understood that the present invention is not limited thereto.

Figure 1:
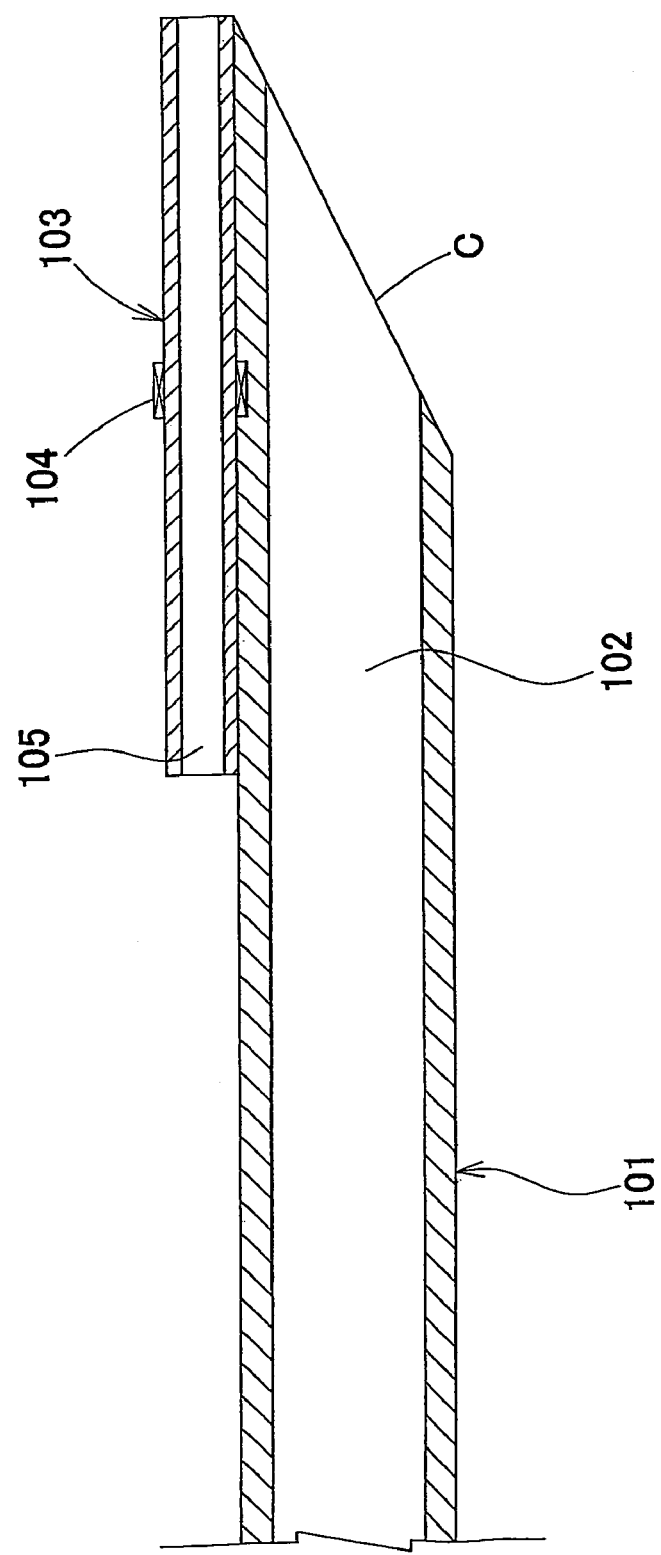
FIG. 1 is a cross-sectional view showing a tip portion of an aspiration catheter in an embodiment of the present invention.
Figure 2:
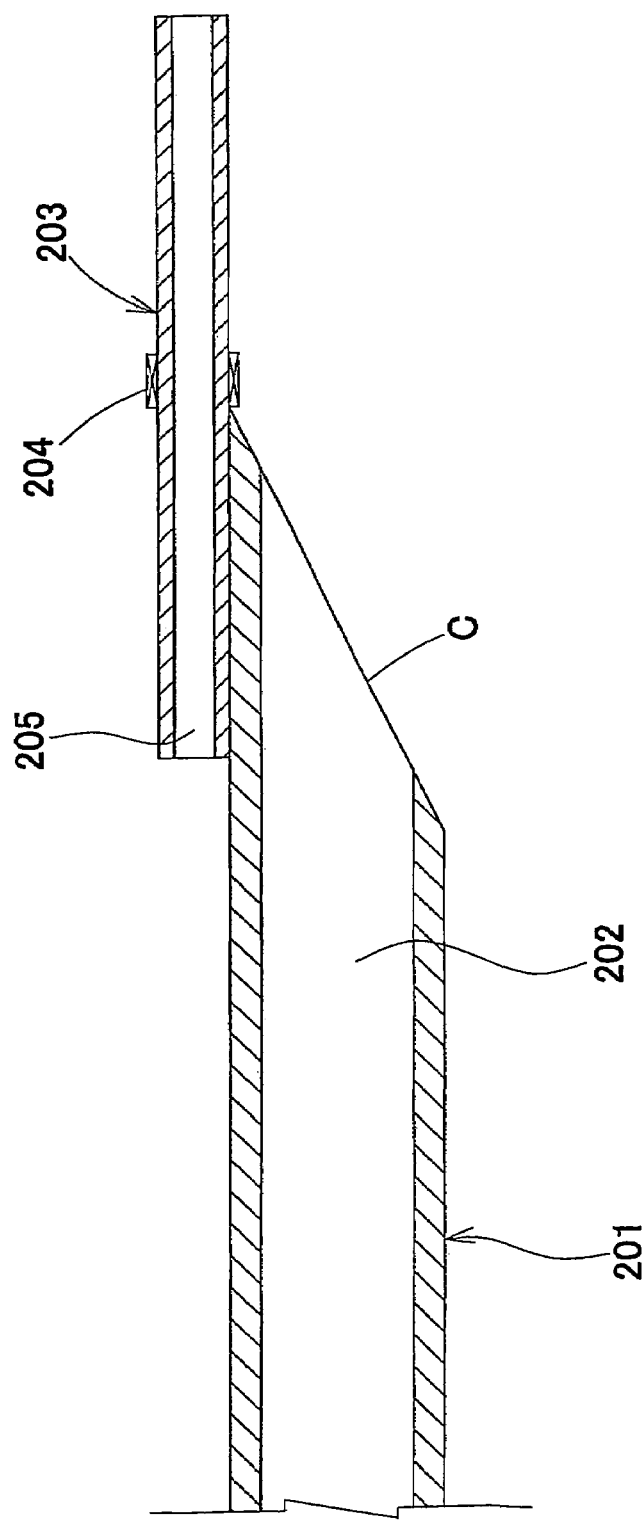
FIG. 2 is a cross-sectional view showing a tip portion of an aspiration catheter in another embodiment of the present invention.
Figure 3:
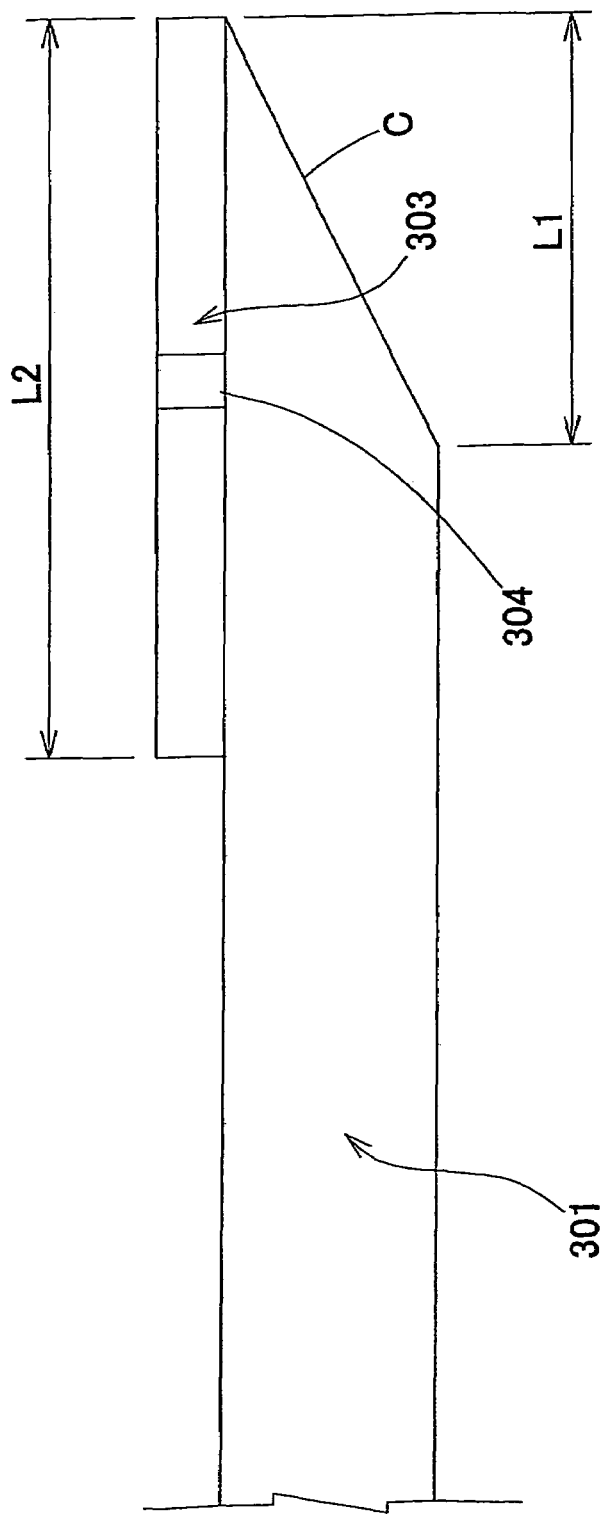
FIG. 3 is a side view showing a tip portion of an aspiration catheter in another embodiment of the present invention.
Figure 4:
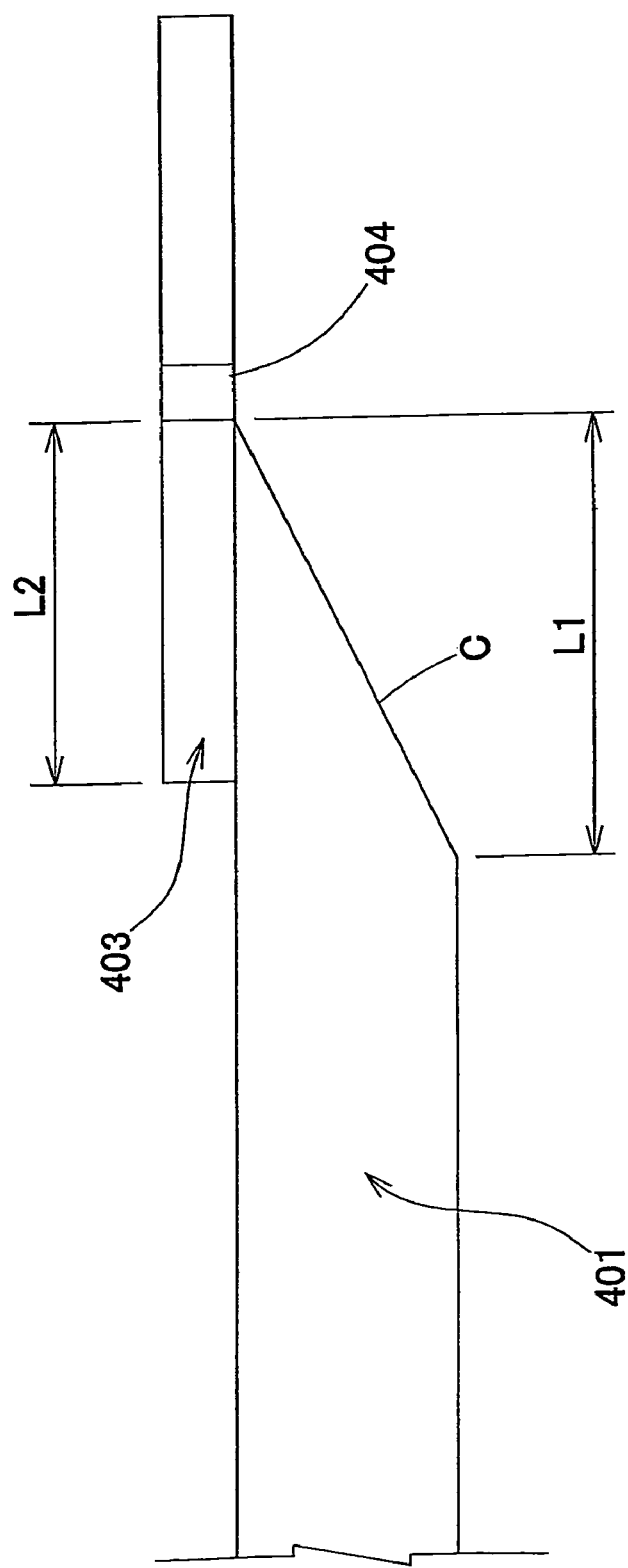
FIG. 4 is a side view showing a tip portion of an aspiration catheter in another embodiment of the present invention.

An aspiration catheter of the present invention includes a main shaft (101, 201, 301, 401, or 501) having an aspiration lumen (102 or 202) disposed therein, the aspiration lumen extending from the proximal end to the distal end of the main shaft; a guidewire shaft (103, 203, 303, 403, or 503) having a guidewire lumen (105 or 205) disposed therein, the guidewire lumen following a guidewire, the guidewire shaft being disposed at the distal end of the main shaft; and a hub disposed at the proximal end of the main shaft (101, 201, 301, 401, or 501). The tip of the main shaft (101, 201, 301, 401, or 501) is obliquely cut. The distal end of the guidewire shaft (103, 203, 303, 403, or 503) is positioned at the distal end of the main shaft (101, 201, 301, 401, or 501) or protrudes from the distal end of the main shaft in the distal direction. The relationships $0.5 \leq L2/L1$ and $L2-L1 \leq 5$ mm are satisfied, wherein L1 is the length of the obliquely cut portion of the main shaft (101, 201, 301, 401, or 501) in the longitudinal direction of the catheter, and L2 is the length from the proximal end of the guidewire shaft (103, 203, 303, 403, or 503) to the distal end of the main shaft (101, 201, 301, 401, or 501). In each of FIGS. 1 and 3, the distal end of the guidewire shaft (103 or 303) is positioned at the distal end of the main shaft (101 or 301). In each of FIGS. 2 and 4, the distal end of the guidewire shaft (203 or 403) protrudes from the distal end of the main shaft (201 or 401) in the distal direction. Reference symbol C in the drawing represents the obliquely cut portion of the main shaft (101, 201, 301, 401, or 501).

Since the guidewire lumen (105 or 205) is disposed at the tip portion of the aspiration catheter, it is possible to advance a guidewire, which the operator performing an angioplasty is accustomed to using, to the periphery of the lesion first. Subsequently, the aspiration catheter of the present invention can be delivered along the guidewire. Delivery of the aspiration catheter along the guidewire also enables treatment of highly tortuous portions and bifurcations in the coronary artery and cerebral blood vessels.

By obliquely cutting the tip of the main shaft (101, 201, 301, 401, or 501) and attaching the guidewire lumen (105 or 205) thereto, an increase in rigidity of the catheter shaft due to the attachment of the guidewire lumen (105 or 205) can be minimized. However, when L2/L1<0.5, if the aspiration catheter is withdrawn under a situation in which another catheter is caught between the tip of the aspiration catheter and the guidewire, the guidewire lumen (105 or 205) of the aspiration catheter becomes easily broken, which is dangerous. When L2−L1>5 mm, the portion in which the guidewire lumen (105 or 205) is attached to the main shaft (101, 201, 301, 401, or 501) is lengthened, and the rigidity of the catheter shaft increases greatly. Consequently, trackability of the aspiration catheter in tortuous blood vessels greatly decreases, which is undesirable. Therefore, the relationships $0.5 \leq L2/L1$ and $L2-L1 \leq 5$ mm are preferably satisfied.

Furthermore, by disposing the guidewire lumen (105 or 205) only on the tip of the main shaft (101, 201, 301, 401, or 501), it is possible to secure a largest possible aspiration lumen (102 or 202). At the proximal side of the guidewire lumen, the guidewire is disposed in parallel with the main shaft.

When the length L1 of the obliquely cut portion C at the tip of the main shaft in the longitudinal direction of the catheter is less than 2 mm, there is a higher risk of damage to the inner wall of the blood vessel by the catheter tip during the advancement of the catheter through the tortuous blood vessel. If the length L1 exceeds 10 mm, it becomes difficult to efficiently remove blood clots by aspiration. Therefore, preferably, the relationship 2 mm$\leq L1 \leq 10$ mm is satisfied.

The advantage of the present invention is not particularly restricted by the method for bonding the guidewire shaft (103, 203, 303, 403, or 503) to the main shaft (101, 201, 301, 401, or 501). Namely, if the guidewire shaft (103, 203, 303, 403, or 503) and the main shaft (101, 201, 301, 401, or 501) are composed of materials that can be welded to each other, bonding can be performed by a known method, such as a heat sealing process. Alternatively, if the guidewire shaft and the main shaft are composed of materials that cannot exhibit sufficient bonding strength when welded, bonding may be performed by a method using an adhesive or the like. In such a case, the chemical species in the adhesive used is not particularly limited. For example, a cyanoacrylate, urethane, epoxy, or silicone adhesive is preferably used. The curing mechanism of the adhesive is also not particularly limited. For example, a moisture-curing, two-part curing, or photo-curable adhesive is preferably used. If the guidewire shaft and the main shaft are composed of materials having poor adhesion properties, surface treatment may be performed, for example, by oxygen plasma or corona discharge, or using a silane coupling agent.

In the catheter, in order to confirm the position of the tip of the catheter by radioscopy, the guidewire shaft (103, 203, 303, 403, or 503) is provided with a radiopaque marker (104, 204, 304, 404, or 504) for confirming the position of the tip of the aspiration catheter by radioscopy. If the radiopaque marker (104, 204, 304, 404, or 504) is provided on the main shaft (101, 201, 301, 401, or 501), the portion provided with the radiopaque marker becomes extremely rigid, resulting in a large decrease in the trackability of the entire catheter. Therefore, the radiopaque marker (104, 204, 304, 404, or 504) having a minimally required size is preferably provided on the guidewire shaft (103, 203, 303, 403, or 503).

The advantage of the present invention is not particularly restricted by the method for attaching the radiopaque marker (104, 204, 304, 404, or 504). Namely, the radiopaque marker may be bonded using an adhesive or the like, physically fixed (by swaging), or attached by any other method. In order to minimize damage to the inner wall of the blood vessel due to the radiopaque marker (104, 204, 304, 404, or 504), preferably, the radiopaque marker (104, 204, 304, 404, or 504) is fixed by swaging and the difference in level between the guidewire shaft (103, 203, 303, 403, or 503) and the radiopaque marker (104, 204, 304, 404, or 504) is reduced as much as possible.

Furthermore, the radiopaque marker (104, 204, 304, 404, or 504) may be composed of any material that shows high visibility under radioscopy. A metal material, such as stainless steel, gold, or platinum, is preferably used for the radiopaque marker. A gold alloy, a platinum alloy, or the like may also be used.

Furthermore, at least a proximal portion of the main shaft (101, 201, 301, 401, or 501) is preferably composed of a high-modulus material with a flexural modulus of 1 GPa or more. By using the shaft composed of such a high-modulus material, power at the proximal end can be fully transmitted to the tip of the catheter, and in addition to the pushing force and the pulling force, the rotating force can be sufficiently transmitted to the tip.

The main shaft (101, 201, 301, 401, or 501) preferably includes two shafts, i.e., a proximal shaft and a distal shaft. The distal shaft is preferably composed of a material having a lower modulus compared with the proximal shaft. Preferred examples of the material for the distal shaft include polyolefins, polyamides, polyesters, polyurethanes, polyolefin elastomers, polyamide elastomers, polyester elastomers, and polyurethane elastomers. Preferred examples of the material for the proximal shaft include polyimides, polyamide-imides, polyether ether ketones, stainless steel, and nickel-titanium alloys. The method for bonding the distal shaft to the proximal shaft is not particularly limited, and a known method, such as welding or adhesion, may be used. Preferably, the change in rigidity at the joint between the distal shaft and the proximal shaft is reduced so that rigidity continuously changes in the longitudinal direction of the aspiration catheter.

Preferably, at least a distal portion of the main shaft (101, 201, 301, 401, or 501) is applied with a hydrophilic coating. In the aspiration catheter, if the size of the aspiration lumen (102, or 202) is increased, the outer diameter of a tube constituting the main shaft (101, 201, 301, 401, or 501) increases, and thereby the sliding friction of the aspiration catheter with the inner wall of the blood vessel increases when the aspiration catheter is inserted into the blood vessel. Therefore, the distal portion of the main shaft (101, 201, 301, 401, or 501) which is highly likely to be inserted into tortuous blood vessels is preferably applied with a hydrophilic coating to reduce sliding friction.

The advantage of the present invention is not particularly restricted by the method for applying the hydrophilic coating and the material for the hydrophilic coating, and the method and the material may be appropriately selected depending on the properties of the main shaft (101, 201, 301, 401, or 501), the guidewire shaft (103, 203, 303, 403, or 503), etc. For example, a hydrophilic polymer, such as poly(2-hydroxyethyl methacrylate), polyacrylamide, or polyvinyl pyrrolidone, is preferably used. Furthermore, by adjusting the thickness of and the material for the hydrophilic coating in the longitudinal direction of the main shaft, the sliding friction can be controlled so as to gradually increase or decrease.

The examples and comparative examples of the present invention will be described in detail below.

EXAMPLE 1

A main shaft was composed of two shafts, i.e., a proximal shaft and a distal shaft. As the proximal shaft, a polyimide tube with an outer diameter of 1.5 mm, an inner diameter of 1.3 mm, and a length of 110 cm was formed by dip forming using a varnish composed of polyamic acid. As the distal shaft, a tube with an outer diameter of 1.5 mm, an inner diameter of 1.2 mm, and a length of 30 cm was formed by extrusion molding using a low-density polyethylene tube (LF480M, Japan Polychem Corporation). The diameter of one end of the proximal shaft was reduced by thermal drawing. The portion in which the diameter was reduced was inserted into the distal shaft and fixed by bonding using a two-part curing urethane adhesive (Nipporan 4235/Coronate 4403, Nippon Polyurethane Industry Co., Ltd.), and the main shaft was thereby obtained. Since the distal shaft was composed of a material with poor adhesion properties, oxygen plasma treatment was performed before bonding.

The tip of the main shaft was cut with a razor so that the length L1 in the longitudinal direction of the catheter was 2 mm.

A tube with an outer diameter of 0.6 mm, an inner diameter of 0.42 mm, and a length of 10 mm was formed by extrusion molding using a high-density polyethylene (HY540, Japan Polychem Corporation), and a radiopaque marker composed of platinum with an outer diameter of 0.72 mm and an inner diameter of 0.65 mm was fixed by swaging on the center of the tube. A guidewire shaft was thereby formed. The guidewire shaft and the main shaft were placed so that the length L2 was 1 mm (refer to FIG. 4), and bonded to each other by heat sealing. During bonding, in order to secure a guidewire lumen and an aspiration lumen, protective mandrels were inserted into both shafts.

A hub formed by injection molding using polycarbonate (Makloron 2658, Bayer AG) was fixed on the proximal end of the main shaft by bonding using a two-part curing urethane adhesive (Nipporan 4235/Coronate 4403, Nippon Polyurethane Industry Co., Ltd.). An aspiration catheter was thereby produced.

EXAMPLE 2

A catheter was produced as in Example 1 except that L1 was set at 2 mm and L2 was set at 4 mm.

EXAMPLE 3

A catheter was produced as in Example 1 except that L1 was set at 2 mm and L2 was set at 7 mm.

EXAMPLE 4

A catheter was produced as in Example 1 except that the length of the guidewire shaft was set at 35 mm, L1 was set at 10 mm, and L2 was set at 5 mm.

EXAMPLE 5

A catheter was produced as in Example 3 except that L1 was set at 10 mm and L2 was set at 15 mm.

COMPARATIVE EXAMPLE 1

A catheter was produced as in Example 1 except that L1 was set at 2 mm and L2 was set at 0.2 mm.

COMPARATIVE EXAMPLE 2

A catheter was produced as in Example 1 except that L1 was set at 2 mm and L2 was set at 10 mm.

COMPARATIVE EXAMPLE 3

A catheter was produced as in Example 3 except that L1 was set at 10 mm and L2 was set at 2 mm.

COMPARATIVE EXAMPLE 4

A catheter was produced as in Example 3 except that L1 was set at 10 mm and L2 was set at 20 mm.

(Evaluation of Bonding Strength Between the Main Shaft and Guidewire Shaft)

Figure 5:
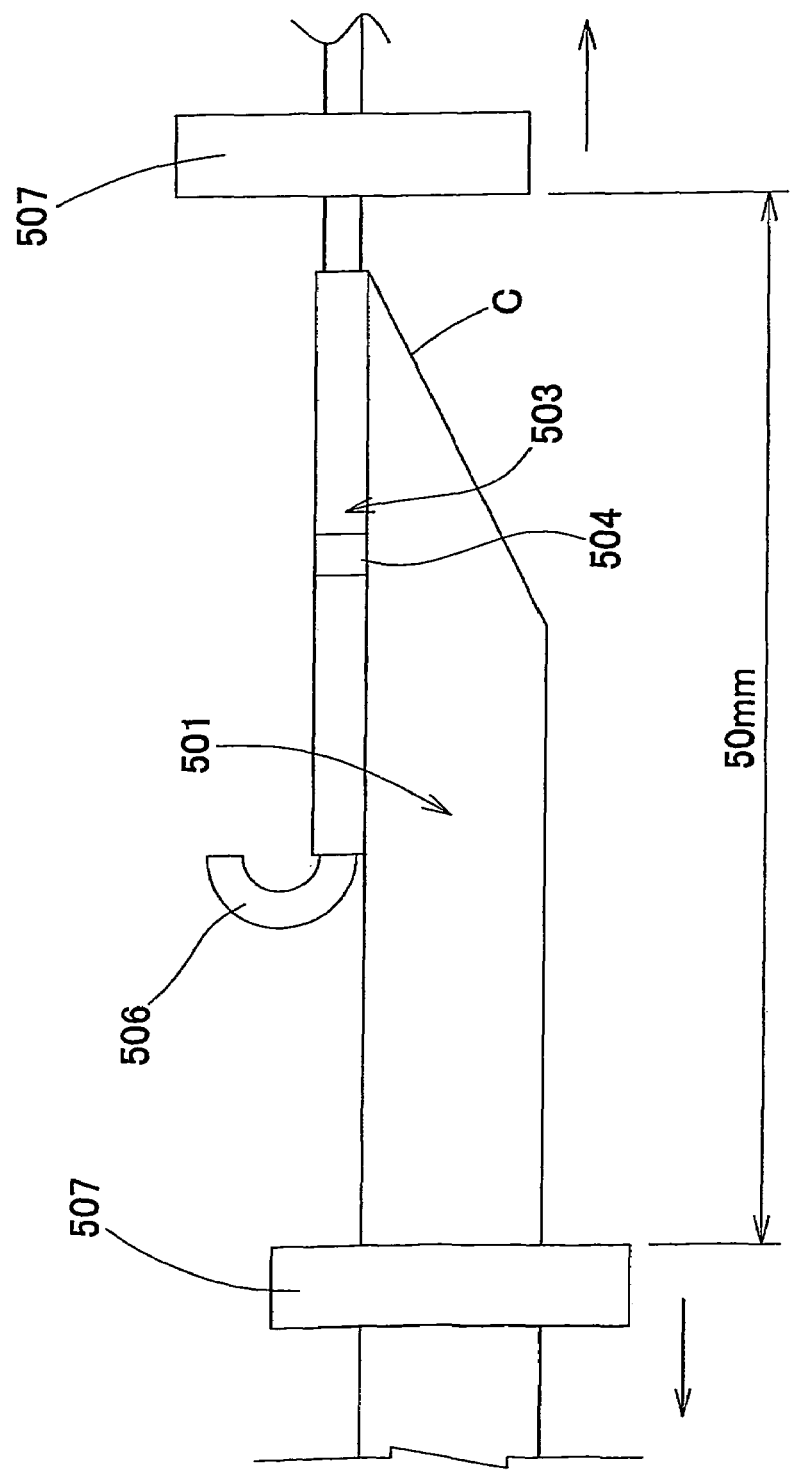
FIG. 5 is a schematic diagram showing a method for evaluating the strength of aspiration catheters in the present invention.

As shown in FIG. 5, the catheter in each of the examples and comparative examples was fastened with fasteners 507 of a tensile tester with a mandrel 506 having an arc-shaped end being inserted into a guidewire shaft 503. The fasteners 507 were spaced at 50 mm, and the tensile test was performed at a rate of 50 mm/min to measure the bonding strength between the main shaft and the guidewire shaft. With respect to each of the examples and comparative examples, measurement was performed with n=3, and the mean value was considered as the measured value. The results thereof are shown in Table 1.

TABLE 1

Evaluation of bonding strength between the main shaft and guidewire shaft

|  | L1 (mm) | L2 (mm) | L2/L1 | L2 − L1 (mm) | Bonding strength (N) | Trackability |
|---|---|---|---|---|---|---|
| Example 1 | 2 | 1 | 0.5 | −1.0 | 6.2 | Satisfactory |
| Example 2 | 2 | 4 | 2.0 | 2.0 | 11.8 | Satisfactory |
| Example 3 | 2 | 7 | 3.5 | 5.0 | 12.3 | Satisfactory |
| Example 4 | 10 | 5 | 0.5 | −5.0 | 6.6 | Satisfactory |
| Example 5 | 10 | 15 | 1.5 | 5.0 | 12.1 | Satisfactory |
| Comparative Example 1 | 2 | 0.2 | 0.1 | −1.8 | 1.7 | Satisfactory Did not pass through bent portion |
| Comparative Example 2 | 2 | 10 | 5.0 | 8.0 | 11.5 | Kinking occurred in catheter |
| Comparative Example 3 | 10 | 2 | 0.2 | −8.0 | 2.9 | Satisfactory Did not pass through bent portion |
| Comparative Example 4 | 10 | 20 | 2.0 | 10.0 | 11.9 | Kinking occurred in catheter |

(Trackability Measurement in Tortuous Blood Vessel)

Figure 6:
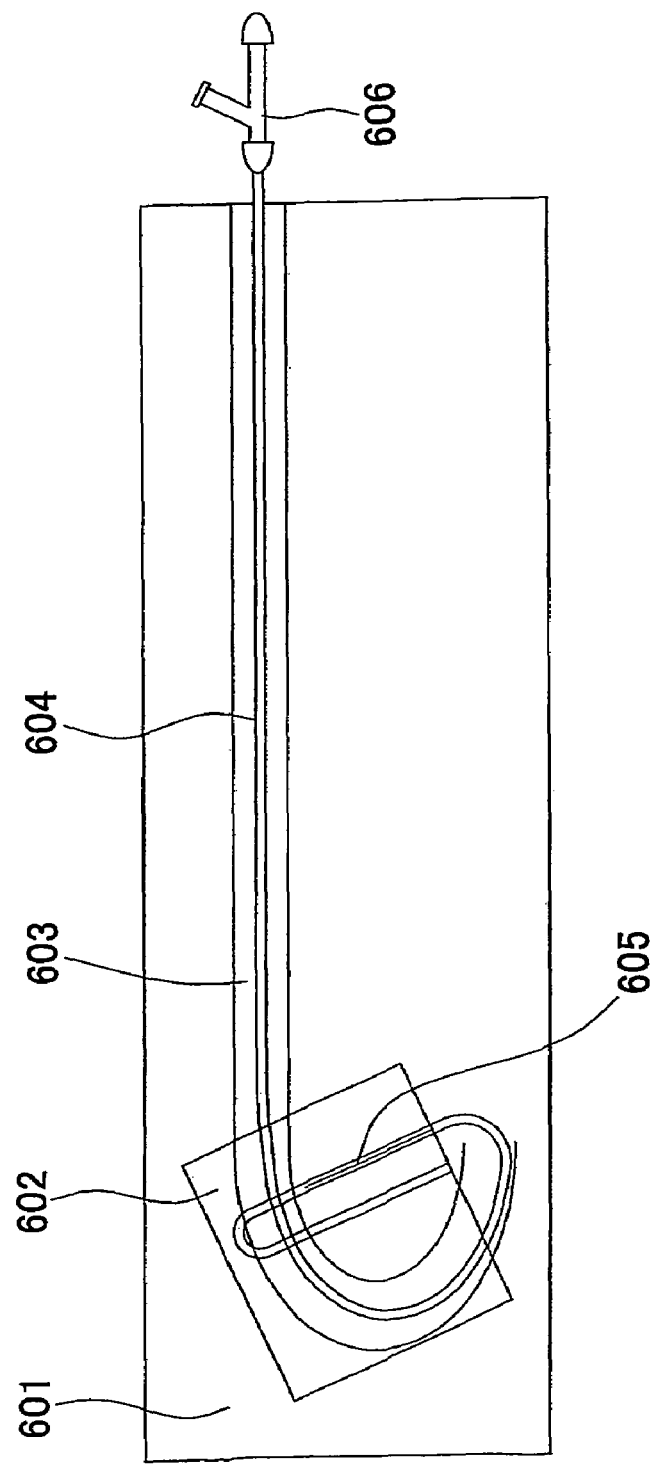
FIG. 6 is a schematic diagram showing a trackability measurement apparatus for aspiration catheters in the present invention.
Figure 7:
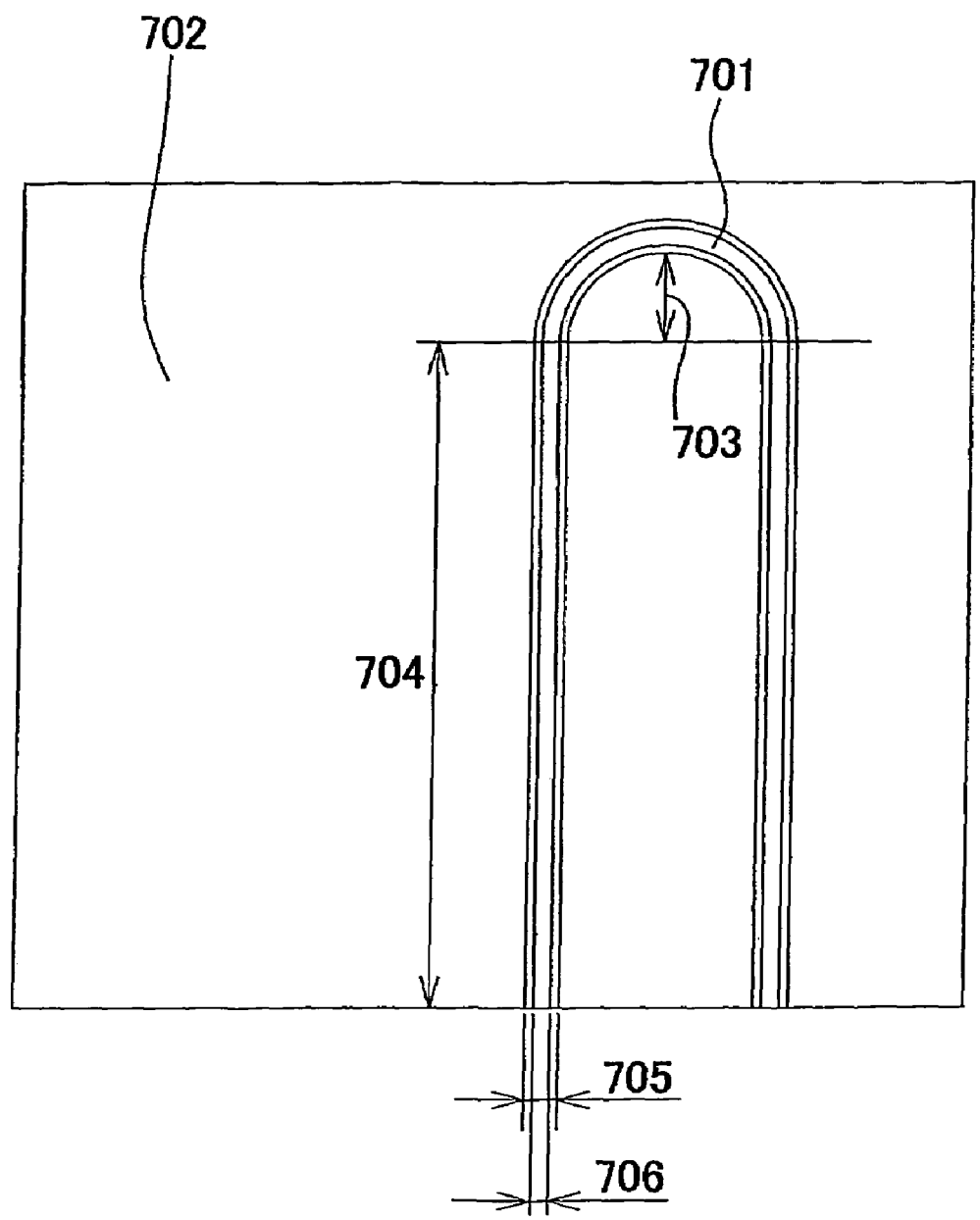
FIG. 7 is an enlarged view of a plate including curved portions shown in FIG. 6.

As shown in FIG. 6, a simulated aorta 603 and a guiding catheter 604 were disposed in a tank 601 filled with a physiological saline solution kept at 37° C., and a hemostasis valve 606 was fixed to the guiding catheter 604. The tip of the guiding catheter 604 was connected to a plate 602 provided with a simulated coronary artery, and a guidewire 605 of 0.014" (0.3556 mm) was preliminarily passed through the guiding catheter 604. As shown in FIG. 7, a polyethylene tube 701 serving as a simulated coronary artery was disposed in a plate 702, and the polyethylene tube 701 included a bent portion 703 and a linear portion 704. The bent portion 703 had a radius of curvature of 15 mm, and the linear portion 704 had a length of 80 mm. The polyethylene tube 701 had an outer diameter 705 of 5 mm and an inner diameter 706 of 3 mm. Each of the aspiration catheters in the examples and comparative examples was inserted into the guiding catheter 604 from the hemostasis valve 606 and passed along the guidewire 605, and the operability thereof was measured. The results are shown in Table 1.

In each of Examples 1 to 5 of the present invention, the bonding strength between the main shaft and the guidewire shaft is sufficiently high at 6.2 N to 12.3 N, and even if another catheter is caught between the tip of the aspiration catheter and the guidewire, it is possible to safely operate the aspiration catheter without breaking of the guidewire lumen. Furthermore, trackability in the bent portion of blood vessel is satisfactory and good operability is shown. Therefore, these aspiration catheters are considered to have high performance.

On the other hand, in each of Comparative Examples 1 and 3, although sufficient trackability in the bent portion of the simulated blood vessel is shown, the bonding strength is extremely low at 1.7 N to 2.9 N. Therefore, safe operation is not ensured.

In each of Comparative Examples 2 and 4, the bonding strength between the main shaft and the guidewire shaft is high at 11.5 N to 11.9 N, and safe operation is performed. However, with respect to the trackability evaluation using the simulated bent blood vessel, it was not possible to advance the catheter over the bent portion, and kinking occurred in the main shaft. The reason for this is believed to be due to an increase in rigidity at the joint between the main shaft and the guidewire shaft.

INDUSTRIAL APPLICABILITY

As described above, the present invention can easily provide an aspiration catheter including a main shaft having an aspiration lumen disposed therein, the aspiration lumen extending from the proximal end to the distal end of the main shaft; a guidewire shaft having a guidewire lumen disposed therein, the guidewire lumen following a guidewire, the guidewire shaft being disposed at the distal end of the main shaft; and a hub disposed at the proximal end of the main shaft, wherein the tip of the main shaft is obliquely cut, the distal end of the guidewire shaft is positioned at the distal end of the main shaft or protrudes from the distal end of the main shaft in the distal direction, and the relationships $0.5 \leq L2/L1$ and $L2-L1 \leq 5$ mm are satisfied, wherein L1 is the length of the obliquely cut portion of the main shaft in the longitudinal direction of the catheter, and L2 is the length from the proximal end of the guidewire shaft to the distal end of the main shaft. In the aspiration catheter, the largest possible aspiration lumen can be secured, and sufficient flexibility is achieved which allows the catheter to track tortuous blood vessels along the guidewire.

The invention claimed is:

1. An aspiration catheter comprising:
    a main shaft having an aspiration lumen disposed therein, the aspiration lumen extending from the proximal end to the distal end of the main shaft;
    a guidewire shaft having a guidewire lumen disposed therein, the guidewire lumen following a guidewire, the guidewire shaft being disposed at the distal end of the main shaft; and
    a hub disposed at the proximal end of the main shaft,
    wherein the tip of the main shaft is obliquely cut, the distal end of the guidewire shaft is positioned at the distal end of the main shaft or protrudes from the distal end of the main shaft in the distal direction, and the relationships 2 mm $\leq L1 \leq 10$ mm, 1 mm $\leq L2 \leq 15$ mm, $0.5 \leq L2/L1$ and $L2-L1 \leq 5$ mm are satisfied, wherein L1 is the length of the obliquely cut portion of the main shaft in the longitudinal direction of the catheter, and L2 is the length from the proximal end of the guidewire shaft to the distal end of the main shaft,
    wherein the main shaft comprises two shafts of a proximal shaft and a distal shaft, wherein the distal shaft is composed of a material having a lower modulus compared with the proximal shaft, and
    wherein the material for the distal shaft comprises polyolefins, polyamides, polyesters, polyurethanes, polyolefin elastomers, polyamide elastomers, polyester elastomers, and polyurethane elastomers, and the material for the proximal shaft comprises polyimides, polyamide-imides, polyether ether ketones, stainless steel, and nickel-titanium alloys.

2. The aspiration catheter according to claim 1, wherein the guidewire shaft is provided with a radiopaque marker for confirming the position of the tip of the main shaft by radioscopy.

3. The aspiration catheter according to claim 1, wherein at least a proximal portion of the main shaft has a flexural modulus of 1 GPa or more.

4. The aspiration catheter according to claim 2, wherein at least a proximal portion of the main shaft has a flexural modulus of 1 GPa or more.

5. The aspiration catheter according to claim 1, wherein at least a distal portion of the main shaft is applied with a hydrophilic coating.

6. The aspiration catheter according to claim 2, wherein at least a distal portion of the main shaft is applied with a hydrophilic coating.

7. The aspiration catheter according to claim 3, wherein at least a distal portion of the main shaft is applied with a hydrophilic coating.

8. The aspiration catheter according to claim 4, wherein at least a distal portion of the main shaft is applied with a hydrophilic coating.

* * * * *